US009187519B1

(12) United States Patent
Slocik et al.

(10) Patent No.: US 9,187,519 B1
(45) Date of Patent: Nov. 17, 2015

(54) REACTIVE NANOCOMPOSITES AND METHODS OF MAKING THE SAME

(71) Applicant: The United States of America, as represented by the Secretary of the Air Force, Washington, DC (US)

(72) Inventors: Joseph M Slocik, Dayton, OH (US); Christopher A Krouse, Bellbrook, OH (US); Rajesh R Naik, Centerville, OH (US)

(73) Assignee: THE UNITED STATES OF AMERICA AS REPRESENTED BY THE SECRETARY OF THE AIR FORCE, Washington, DC (US)

( * ) Notice: Subject to any disclaimer, the term of this patent is extended or adjusted under 35 U.S.C. 154(b) by 453 days.

(21) Appl. No.: 13/729,100

(22) Filed: Dec. 28, 2012

(51) Int. Cl.
| | | |
|---|---|---|
| C07K 14/00 | (2006.01) |
| C07K 1/107 | (2006.01) |
| B05D 7/00 | (2006.01) |
| B82Y 40/00 | (2011.01) |
| B82Y 30/00 | (2011.01) |
| C07K 14/47 | (2006.01) |

(52) U.S. Cl.
CPC ............... *C07K 1/1077* (2013.01); *B05D 7/52* (2013.01); *B05D 7/56* (2013.01); *B82Y 30/00* (2013.01); *B82Y 40/00* (2013.01); *C07K 14/47* (2013.01); *B05D 2202/20* (2013.01); *B05D 2202/25* (2013.01); *B05D 2202/35* (2013.01)

(58) Field of Classification Search
None
See application file for complete search history.

(56) References Cited

U.S. PATENT DOCUMENTS

| 6,984,386 | B2 | 1/2006 | Douglas et al. |
| 7,219,017 | B2 | 5/2007 | Vitaliano et al. |
| 7,393,924 | B2 | 7/2008 | Vitaliano et al. |
| 7,816,491 | B2 | 10/2010 | Trent et al. |
| 2004/0028694 | A1 | 2/2004 | Young et al. |
| 2010/0029910 | A1* | 2/2010 | Shiba et al. .................. 530/400 |
| 2012/0020879 | A1 | 1/2012 | Watt |

OTHER PUBLICATIONS

Cotez et al, Journal of Applied Physics, 111, 124311-5, published online Jun. 21, 2012.*
Kramer et al, Mat. Res. Soc. Symp. Proc. vol. 776, pp. Q9.6.1-Q9.6.6, 2003.*
Kim, Jae-Woo, et al., "Biologically Derived Nanoparticle Arrays via a Site-Specific Reconstitution of Ferritin and their Electrochemistry," NASA Technical Report, 206th Meeting of the Electrochemical Society, Oct. 3-8, 2004, Honolulu, HI [available at http://ntrs.nasa.gov/archive/nasa/casi.ntrs.nasa.gov/20040161140_2004158757.pdf].
Bogdanovic, Goran, et al., "Formation and Structure of Polyelectrolyte and Nanoparticle Multilayers: Effect of Particle Characteristics," Journal of Colloid and Interface Science 255, 44-51 (2002).
McMillan, R. Andrew, et al., "A robust and engineerable self-assembling protein template for the synthesis and patterning of ordered nanoparticle arrays," NASA Technical Report (2004) [available at http://ntrs.nasa.gov/archive/nasa/casi.ntrs.nasa.gov/20050010138_2005000117.pdf].

(Continued)

*Primary Examiner* — Erma Cameron
(74) *Attorney, Agent, or Firm* — AFMCLO/JAZ; James P. Carey

(57) ABSTRACT

Reactive nanocomposites comprising a metal nanoparticle functionalized with one or more layers of self-assembled protein cages and methods of making the same. The reactive nanocomposites according to the present invention demonstrate improved reaction kinetics and enhanced exothermic behavior.

15 Claims, 7 Drawing Sheets

(56) References Cited

OTHER PUBLICATIONS

Kim, Jae-Woo, et al., "Electrochemically controlled reconstitution of immobilized ferritins for bioelectronic applications," Journal of Electroanalytical Chemistry, vol. 601, Issues 1-2, pp. 8-16 (2007).
Flenniken, M.L., et al., "A Library of Protein Cage Architectures as Nanomaterials," Current Topics in Microbiology and Immunology 327, pp. 71-93 (2009).
Slocik, Joseph M. and Naik, Rajesh R., "Biological Assembly of Hybrid Inorganic Nanomaterials," Current Nanoscience, vol. 3, issue 2, pp. 117-120 (2007).
Caruso, Frank, "Nanoengineering of Particle Surfaces," Advanced Materials 13, No. 1, pp. 11-22 (2001).
Dickerson, Matthew B., et al., "Protein- and Peptide-Directed Syntheses of Inorganic Materials," Chem. Rev. 2008, 108, 4935-4978 (2008).
Chirea, Mariana, et al., "Electrochemical Characterization of Polyelectrolyte/Gold Nanoparticle Multilayers Self-Assembled on Gold Electrodes," J. Phys. Chem. B 109, 21808-21817 (2005).
Chen, Chao, et al., "Nanoparticle-Templated Assembly of Viral Protein Cages," Nano Letters, vol. 6, No. 4, pp. 611-615 (2006).
Heddle, Jonathan G., "Protein cages, rings and tubes: useful components of future nanodevices?," Nanotechnology, Science and Applications 1, pp. 67-78 (2008).
Uchida, Masaki, et al., "Biological Containers: Protein Cages as Multifunctional Nanoplatforms," Advanced Materials, 19, pp. 1025-1042 (2007).
Sana, Barindra, et al., "Iron-Based Ferritin Nanocore as a Contrast Agent," Biointerphases 5 (3) pp. FA 48-52 (2010).
Kobayashi, Mime, et al., "A water-soluble carbon nanotube network conjugated by nanoparticles with defined nanometre gaps," Chem. Commun., 47, 3475-3477 (2011).
Sang, Ken-Ichi and Shiba, Kiyotaka, "In Aqua Manufacturing of a Three-Dimensional Nanostructure Using a Peptide Aptamer," MRS Bulletin, vol. 33, pp. 524-529 (May 2008) available at [www.mrs.org/bulletin].
Andrews, Simon C.; "The Ferritin-like superfamily: Evolution of the biological iron storeman from a rubrerythrin-like ancestor." Biochimica et Biophysica Acta, 1800 (2010) 691-705.

\* cited by examiner

REACTIVE NANOCOMPOSITES AND METHODS OF MAKING THE SAME

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of energetic nanomaterials. More particularly, it relates to reactive nanocomposites comprising functionalized metal nanoparticles and methods of making the same.

2. Description of the Related Art

Proteins such as ferritin that form protein cages have been used in a variety of nanocomposite materials. For example, protein cages have been used for the confined synthesis of monodisperse Au, Ag, CdS, Pd, $TiO_2$, $Fe_3O_4$, and $UO_2$ nanoparticles by adding a nanoparticle-binding peptide. In addition, protein cages have been used in the molecular transport/storage of small molecules for drug delivery and for assembly on titania, carbon nanotube, and gold surfaces by addition of a metal-binding peptide on the exterior cage. In these assemblies, the close proximity of ferritin to the nanomaterial surface resulted in enhanced optical and electrical properties.

The use of nanoparticles to fabricate reactive nanocomposites combines the high reaction rates of molecular explosives and materials with the high energy density of composite materials. However, the performance of many nanomaterials-based energetic formulations often suffers from poor mass transport, uneven distribution of nanocomposite components, and large diffusion distances. In addition, conventional methods of manufacturing reactive nanocomposites often encounter a number of problems associated with safe handling and processing of the materials such as their propensity toward decomposition and instability and sensitivity of the reactive components. Several methods such as powder compaction, melt blending, and solution mixing that attempt to achieve a uniform nanocomposite have met with limited success and are still plagued with poor chemical and physical interaction between the components of the nanocomposite.

SUMMARY OF THE INVENTION

The present invention includes a method of making a reactive nanocomposite comprising the steps of: loading positively-charged protein cages with one or more types of oxidizer to form loaded positively-charged protein cages, with the oxidizer being loaded into the pores of the positively-charged protein cages; and assembling the loaded positively-charged protein cages onto an outer surface of metal nanoparticles to form the reactive nanocomposite.

In one embodiment of the method, the metal nanoparticles are Al, B, Si, Mg, Ni, Ti, and/or Ag. In another embodiment, the oxidizer is iron oxide and/or ammonium perchlorate. In a further embodiment, the positively-charged protein cages are ferritin, heat shock proteins, capsid proteins, and/or ferritin-like proteins. In an alternative embodiment, the positively-charged protein cages further comprise a chemical oxidizing agent, a non-ferric metal oxide, a molecular explosive, and/or a fluorescent dye taggant.

The present invention further includes a method of making a multi-layer reactive nanocomposite comprising alternating layers of oppositely-charged loaded protein cages. The method comprises the steps of: loading positively-charged protein cages with one or more types of oxidizer to form loaded positively-charged protein cages, with the oxidizer being loaded into the pores of the positively-charged protein cages; assembling the loaded positively-charged protein cages onto an outer surface of metal nanoparticles to form a one-layer reactive nanocomposite; loading negatively-charged protein cages with one or more types of oxidizer to form loaded negatively-charged protein cages, with the oxidizer being loaded into the pores of the negatively-charged protein cages; assembling the loaded negatively-charged protein cages onto the one-layer reactive nanocomposite to form a two-layer reactive nanocomposite; and adding alternating layers of loaded positively-charged protein cages and loaded negatively-charged protein cages to achieve the multi-layer reactive nanocomposite having a desired composition and a desired number of layers.

In one embodiment of the method, the metal nanoparticles are Al, B, Si, Mg, Ni, Ti, and/or Ag. In another embodiment, the oxidizer is iron oxide and/or ammonium perchlorate. In a further embodiment, the positively-charged protein cages are ferritin, heat shock proteins, capsid proteins, and/or ferritin-like proteins. In an alternative embodiment, the positively-charged protein cages further comprise a chemical oxidizing agent, a non-ferric metal oxide, a molecular explosive, and/or a fluorescent dye taggant.

The present invention further includes a method of making a multi-layer hybrid reactive nanocomposite comprising alternating layers of at least one of oppositely-charged loaded protein cages and negatively-charged polyelectrolyte complexes. The method comprises the steps of: loading positively-charged protein cages with one or more types of oxidizer to form loaded positively-charged protein cages, with the oxidizer being loaded into the pores of the positively-charged protein cages; assembling the loaded positively-charged protein cages onto an outer surface of metal nanoparticles to form a one-layer reactive nanocomposite; coating at least one type of oxidizer with a negatively-charged polyelectrolytes to form negatively-charged polyelectrolyte complexes; assembling the negatively-charged polyelectrolyte complexes onto the one-layer reactive nanocomposite to form a two-layer hybrid reactive nanocomposite; and adding alternating layers of at least one of loaded positively-charged protein cages, loaded negatively-charged protein cages, and negatively-charged polyelectrolyte complexes to achieve a multi-layer hybrid reactive nanocomposite having a desired composition and a desired number of layers.

In one embodiment of the method, the metal nanoparticles are Al, B, Si, Mg, Ni, Ti, and/or Ag. In another embodiment, the oxidizer is iron oxide and/or ammonium perchlorate.

In an alternative embodiment, the method of making a multi-layer hybrid reactive nanocomposite further comprises site-directed assembly comprising the steps of: coating a surface with negatively-charged polyelectrolytes, in which the surface has a desired location; and assembling the one-layer reactive nanocomposite onto the negatively-charged polyelectrolytes, thereby directing assembly of the multi-layer hybrid reactive nanocomposite onto the surface in the desired location.

DETAILED DESCRIPTION OF THE INVENTION

Figure 1A:
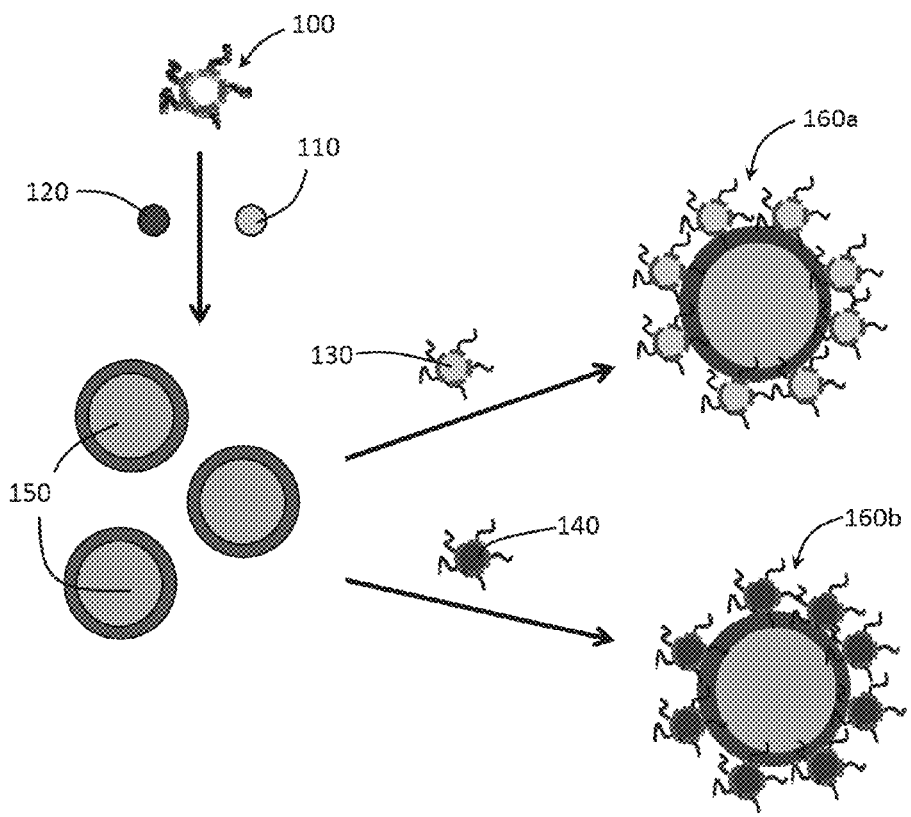
FIG. 1A is a depiction of one embodiment of a single-layer reactive nanocomposite.

The present invention includes reactive nanocomposites comprising a nanoparticle functionalized with one or more layers of self-assembled proteins and/or protein cages and methods of making the same. The present invention takes advantage of assembly strategies derived from biology and the high affinity of biomolecules for inorganic materials to direct the layer-by-layer (LBL) assembly of oxidizer-loaded protein cages onto the surface of metal nanoparticles. The resulting reactive nanocomposites demonstrate improved reaction kinetics, due in part to the reduction in the diffusion distance between the reactants and the increased stability of the oxidizing agent inside the protein cage. The ability to tailor the number and composition of the protein layers may be used to control and optimize stoichiometric conditions, thereby tuning and maximizing energetic performance. The result is a stoichiometrically balanced energetic reaction in which substantially all of the reactive metal may be consumed. The reactive nanocomposites according to the present invention demonstrate enhanced exothermic behavior in comparison to other reactive materials such as nanothermite mixtures of bulk nano-Al with free ammonium perchlorate and/or micron- and nano-sized iron oxide powders prepared without the use of ferritin.

In one embodiment of the present invention, an improved reactive nanocomposite may be fabricated by loading protein cages with an oxidizer and assembling one or more layers of the loaded protein cages onto the surface of a reactive metal nanoparticle. The nanometal may be any suitable energetic material including Al, B, Si, Mg, Ni, Ti, and Ag, with Al being one of the most common. The assembled nanocomposite may comprise one type of metal or a combination of metals to create a heterogeneous complex. Reactive metals contain and release a large amount of stored energy due to their chemical composition and size. As a result, they are regularly used in propellants, explosives, and pyrotechnics. Many conventional formulations utilize micron-scale reactive metal powders as fuel and/or additives to achieve and improve combustion efficiency and energy output. Alternatively, metal prepared as a nanopowder such as nano-aluminum (nano-Al) is of particular interest as an energetic material because of its superior properties and processability. Nanometals generally have a higher energy density than organic explosives and a higher specific surface area as compared to micron-sized metal powders. In addition, energetic nanometals are amenable to functionalization and assembly with other reactive materials, and they often contain a thin oxide layer, which makes them less pyrophoric. All of these properties contribute to the potential for enhanced rates of reaction for composites comprising nanometals.

A protein cage comprises multiple protein units that self assemble into a cage surrounding a central cavity. Ferritins are an important family of highly-conserved, globular proteins that regulate in vivo iron levels, and they one of the most commonly used protein cages. They are typically about 12 nm in diameter, with an internal cavity diameter of about 8 nm Ferritins store reservoirs of $Fe^{3+}$ as a ferrihydrite nanoparticle, $FeO(OH)$, within the hollow protein cavity, releasing Fe ions when needed. The protein is an abundant and inexpensive material that may be obtained recombinantly in high yields or from large ferritin reservoirs found in mammals (i.e. horse spleen).

Ferritin may be modified to improve the binding interaction with the nanometal particle. Three types of ferriting—a chemically modified ferritin cage with a positively charged surface (cationized ferritin), a negatively charged unmodified native ferritin with a carboxylate-rich surface, and a genetically modified protein cage displaying Al-binding peptides— were tested to determine which demonstrated the best binding to nano-Al (data not shown). The cationized ferritin cages showed the highest binding to nano-Al particles, while the genetically modified ferritin cages showed about three-fold less binding to the alumina surface than cationized ferritin by mass. The unmodified native ferritin showed almost no affinity for the nano-Al.

Additional examples of self-assembling proteins that may be used include heat shock proteins, capsid proteins derived from viruses and bacteriophages, and ferritin-like proteins, all of which possess diverse structures, geometries, sizes, and internal cavities (pores). Examples of heat shock proteins may include TF55β (chimeric) and the small heat-shock protein isolated from *Methanococcus jannaschii*. Examples of viruses containing suitable capsid proteins may include the tobacco mosaic virus, brome mosaic virus, iridovirus, the cowpea mosaic virus, and the cowpea chlorotic mottle virus. Suitable bacteriophage capsid proteins may be derived from the MS2, M13, and P22 bacteriophages. In general, viral and bacteriophage capsid proteins tend to be larger, which allows them to encapsulate larger oxidizer molecules and/or additional reactants. Many assembled viral capsids are around 30 nm in diameter, with some reaching 100 nm or more in diameter. Ferritin-like proteins may include Dps proteins (DNA-binding proteins from starved cells) from *Escherichia coli* and an iron-binding protein Dpr from *Streptococcus pyogenes*.

The interior and/or exterior surfaces of the ferritin or other type of protein cage may be further modified by genetic or chemical addition of molecular recognition elements such as peptides, DNA aptamers, and antibodies, as well as fluorophores and polymers. Examples may include the addition of a titanium-binding peptide to the exterior ferritin surface, addition of silver-mineralizing peptides displayed along the interior surface of the protein cage, and introduction of polymeric dendrimer scaffolds of varying sizes synthetically grown from interior surface of a P22 capsid through a radical initiated polymerization mechanism. These modified proteins may be used for a variety of applications, including sensing, binding, tracking, and imaging of various targets such as bacteria, viruses, and chemical warfare agents. In addition, the modified protein cages may be used in the location and neutralization or destruction of targets upon binding and sequestration of the target.

One example of a suitable oxidizer is $NH_4ClO_4$ (ammonium perchlorate, AP), a strong oxidizer that decomposes at low temperatures (<200° C.) and releases energy when mixed with reactive metals such as nano-Al. Another example of a suitable oxidizer is an iron oxide such as ferrihydrite (FeO(OH)), as well different crystalline phases of iron oxide such as ferric oxide or hematite ($Fe_2O_3$) and ferrous ferric oxide or magnetite ($Fe_3O_4$), all of which are herein generally referred to as "iron oxide."

In addition to the oxidizer, the protein cages may optionally contain a variety of additional reactants such as other types of chemical oxidizing agents and non-ferric metal oxides, molecular explosives, and fluorescent dye taggants, and combinations thereof. Examples of chemical oxidizing agents and metal oxides may include $Ag(IO_3)$ (silver iodate), manganese oxide, copper oxide, and boron oxide. Examples of molecular explosives may include trinitrotoluene (TNT) and cyclotrimethylenetrinitramine (RDX). Examples of taggants may include cadmium telluride (CdTe) or cadmium selenide (CdSe) quantum dots and rhodamine fluorescent dyes.

The reactive nanocomposite may optionally comprise one or more polymeric electrolytes (polyelectrolytes). Examples of suitable polyelectrolytes may include, but are not limited to, poly-L-lysine (PLL), polyacrylic acid (PAA), poly(sodium styrene sulfonate) (PSS), poly(allylamine hydrochloride) (PAH), deoxyribonucleic acid (DNA), ribonucleic acid (RNA), and combinations thereof. Polyelectrolytes may be used in place of or in addition to the charged protein cages to create a brick-and-mortar structure or to assist in the directed self-assembly of an energetic formulation. For example, iron oxide coated with a negatively charged polyelectrolyte may be assembled onto nano-Al functionalized with a layer of cationized ferritin. In addition, polyelectrolytes may be used in site-directed assembly, for example, by coating a surface with a negatively charged polyelectrolyte and assembling nano-Al functionalized with a layer of cationized ferritin onto the surface.

Referring now to the drawings, like reference numerals may designate like or corresponding parts throughout the several views. In one embodiment, the reactive nanocomposite may comprise a single layer of protein cages, an example of which is shown in FIG. 1A. Cationized ferritin cages 100 are loaded with an oxidizer, which may be an iron oxide nanoparticle 110 or AP 120, to form an iron oxide-loaded cationized ferritin cage 130 or an AP-loaded cationized ferritin cage 140, respectively. The iron oxide nanoparticles 110 may be in the biologically active form of ferrihydrite, FeO(OH). The iron oxide-loaded cationized ferritin cages 130 or the AP-loaded cationized ferritin cages 140 are then assembled in a single layer onto the outer surface of nano-Al particles 150 to form a single-layer reactive nanocomposite 160a, 160b (see also Example 1). The single-layer reactive nanocomposite 160a comprising iron oxide-loaded cationized ferritin cages 130 is chemically equivalent to thermite (a metal oxide plus a reactive metal) and may be deemed a "bio-thermite."

Figure 1B:
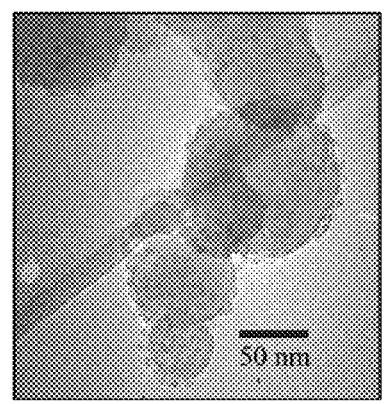
FIG. 1B is a transmission electron microscope (TEM) image of cationized ferritin protein cages filled with an iron oxide core that were assembled onto nano-Al particles.

FIG. 1B is a transmission electron microscope (TEM) image of cationized ferritin protein cages filled with an iron oxide core that were assembled with nano-Al particles (approximately 80 nm) to create a bio-thermite such as the embodiment of a single-layer reactive nanocomposite 160a depicted in FIG. 1A. The pore of each ferritin cage contains a particle that is approximately 6 nm in diameter and is in the biologically active form of ferrihydrite, FeO(OH), as depicted by the dark electron dense cores on the surface of the nano-Al particles in the TEM micrograph. As seen in FIG. 1B, the surface of each nano-Al particle is uniformly decorated with approximately 30-40 ferritin cages.

Figure 2A:
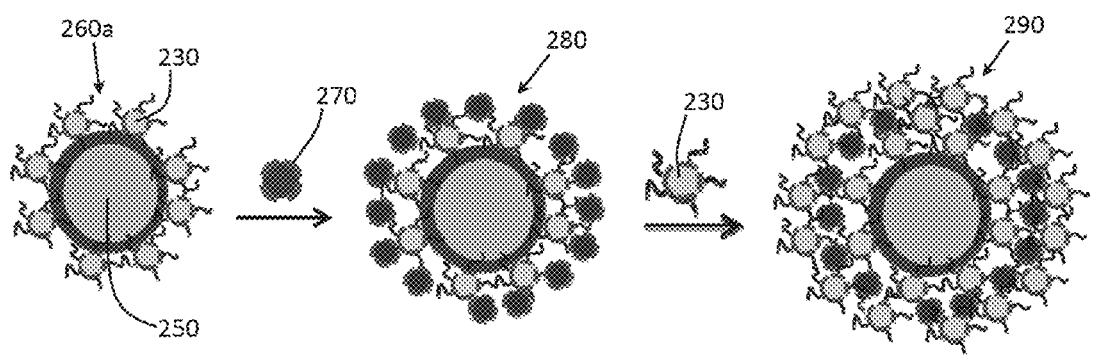
FIG. 2A is a depiction of one embodiment of a multi-layer reactive nanocomposite.
Figure 2B:
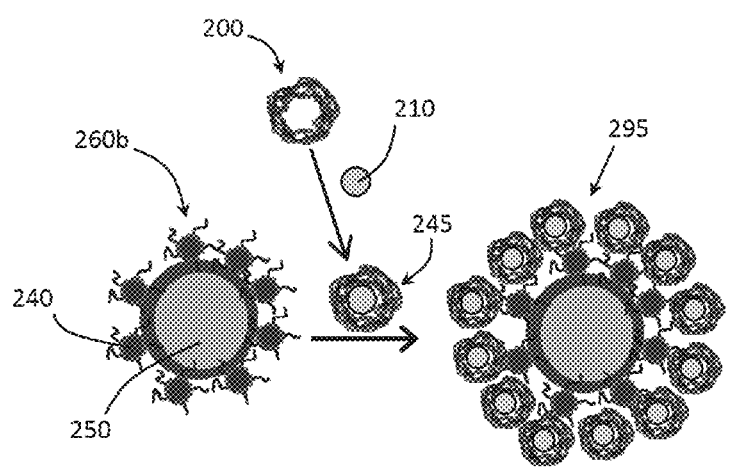
FIG. 2B is a depiction of an alternative embodiment of a multi-layer reactive nanocomposite.
Figure 3A:
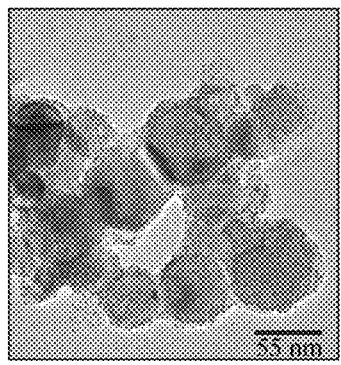
FIGS. 3A-3F are TEM images of single- and multi-layer reactive nanocomposites respectively containing between one and six alternating homogeneous layers of cationized and native ferritin loaded with iron oxide assembled onto nano-Al particles.
Figure 3B:
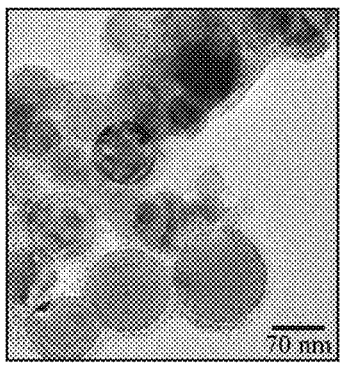
Figure 3C:
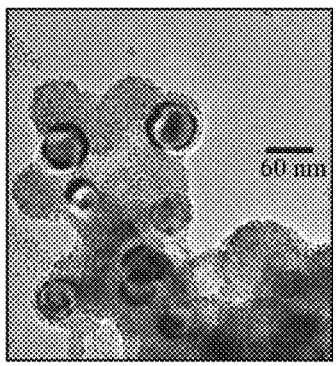
Figure 3D:
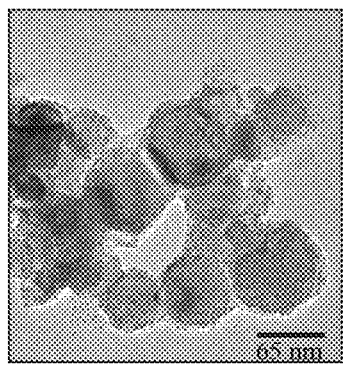
Figure 3E:
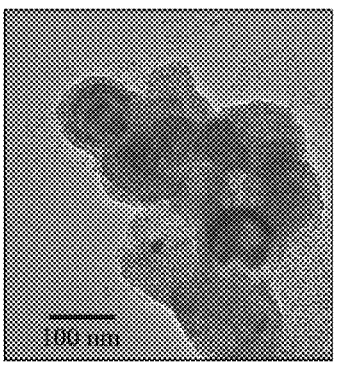
Figure 3F:
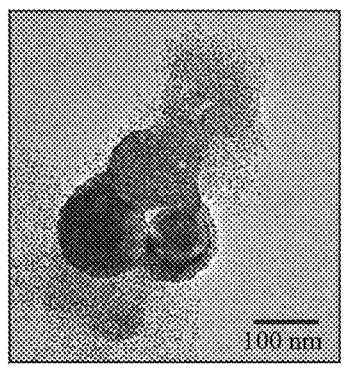

In an alternative embodiment shown in FIGS. 2A and 2B, the reactive nanocomposite according to the present invention may be a multi-layer reactive nanocomposite comprising two or more layers of different types of protein and/or protein cages achieved by a layer-by-layer (LBL) process. As shown in FIG. 2A, loaded cationized ferritin cages 230 loaded with an oxidizer (iron oxide in this example) are assembled in a single layer on the surface of a nano-Al particle 250 to form a single-layer reactive nanocomposite 260a similar to that shown in FIG. 1A. The loaded cationized ferritin cages 230 may have a zeta potential of approximately +23.6±8.0 mV (obtained on a Malvern Instruments® nano series Zeta-sizer®). The loaded cationized ferritin cages 230 interact strongly with the surface of the nano-Al particle 250 and provide an abundance of surface charge for assembly with a second protein layer containing an opposite electrostatic charge. Loaded native (unmodified) ferritin cages 270 loaded with an oxidizer (AP in this example) are then assembled in a single layer on top of the layer of loaded cationized ferritin cages 230 to form a two-layer reactive nanocomposite 280. The loaded native ferritin cages 270 are negatively charged and may have a zeta potential of approximately −32.9±8.7 mV. A layer of loaded cationized ferritin cages 230 (loaded with iron oxide in this example) may be assembled onto the layer of loaded native ferritin cages 270 to form a three-layer reactive nanocomposite 290. Additional alternating layers of (oppositely charged) loaded native ferritin cages 270 and loaded cationized ferritin cages 230 may be added to achieve the desired composition and number of layers.

FIG. 2B depicts an alternative embodiment of a multi-layer hybrid reactive nanocomposite comprising two or more layers of different types of proteins and protein cages achieved by an LBL process. Loaded cationized ferritin cages 240 (loaded with AP in this example) are assembled onto nano-Al particles 250 to form a single-layer reactive nanocomposite 260b similar to that shown in FIG. 1A. An oxidizer (iron oxide 210 in this example) is coated with a negatively charged polyelectrolyte 200 to form a negatively charged polyelectrolyte complex 245, which is then assembled on top of the layer of loaded cationized ferritin cages 240 to form a multi-layer hybrid reactive nanocomposite 295. Similar to the embodiment depicted in FIG. 2A, additional alternating layers of loaded cationized ferritin cages 240, loaded native ferritin cages (not shown), and/or negatively charged polyelectrolyte complexes 295 may be added to achieve the desired composition and number of layers.

FIGS. 3A-F are TEM micrographs (obtained on a Philips CM200 TEM operating at 200 kV) of single- and multi-layer reactive nanocomposites respectively containing between one and six alternating homogeneous layers of cationized and native ferritin loaded only with iron oxide. In total, up to 12 layers of iron oxide loaded ferritin have been successfully loaded onto nano-Al with good coverage (data not shown).

In all embodiments of the reactive nanocomposite according to the present invention, the oxidizer may comprise iron oxide, AP, or both. In one embodiment, the oxidizer comprises all iron oxide. In another embodiment, the oxidizer comprises all AP. In further embodiments such as those depicted in FIGS. 2A and 2B, the oxidizer may comprise iron oxide and AP in alternating layers. The interior protein contents (iron oxide particle or ammonium perchlorate) may also be varied at any layer by sequential addition of AP/dialysis steps as described below in Example 1 or mineralization of the iron oxide inside the protein cage. Different layers of self-assembled proteins containing both iron oxide and AP may further be assembled as heterogeneous layers and/or varied by the assembly order with respect to the nano-Al surface (i.e. AB-nAl or BA-nAl). In addition, different types of oxidizers may be loaded into the same protein cage. The oxidizer may be varied from layer to layer and within the same layer to obtain higher iron oxide loading with nano-Al and to achieve the desired stoichiometric conditions and wt %, thereby achieving a reactive nanocomposite having the desired reactivity.

The following examples and methods are presented as illustrative of the present invention or methods of carrying out the invention and are not restrictive or limiting of the scope of the invention in any manner.

Example 1

Assembly of Single-Layer Ferritin-Nano-Al 2 mg of aluminum nanoparticles (NovaCentrix® Inc., 80 nm, 80% active Al content) passivated with an amorphous aluminum oxide is added to 100 μL of cationized ferritin from horse spleen (Sigma®, 48 mg/mL) containing a core of iron oxide. The mixture is dispersed and sonicated in 500 μL of deionized water. These components are incubated for 1 hour to promote functionalization of the nano-Al with protein cages and then purified to remove excess unbound ferritins by centrifugation at 4000 rpm for 10 minutes. The isolated ferritin-nano-Al pellet is redissolved in 500 μL of deionized water to achieve a single-layer ferritin-nano-Al material similar to that depicted in FIG. 1A.

To obtain AP-loaded ferritin-nano-Al, the iron oxide core of cationized ferritin is removed by reductive dissolution with 0.5% mercaptopropionic acid in 0.1 M acetate buffer, pH 4.5, and repeated dialysis using 10 kDa MWCO dialysis tubing (Fisherbrand®). The empty cage is then subsequently filled via successive additions of 0.1 M ammonium perchlorate (Sigma®) in water and multiple dialysis steps to obtain maximal loading. The result is a single-layer ferritin-nano-Al material similar to that depicted in FIG. 1A. Alternatively, to spectroscopically show incorporation, a rhodamine perchlorate analogue (Exciton®) may be used in place of or along with the AP during loading of the apoferritin cages.

Example 2

LBL Assembly of Multi-Layer Ferritin-Nano-Al

Nano-Al particles are first coated with a single layer of cationized ferritin as described above in Example 1. Following centrifugation to remove excess unbound ferritins and resuspension in deionized water, 100 μL of native ferritin containing an iron oxide core from horse spleen (Sigma®, 56 mg/mL) is added to the single-layer ferritin-nano-Al and incubated for 15 minutes, followed by centrifugation at 4000 rpm for 10 minutes. The pellet is resuspended in 500 μL of deionized water to yield two layers of protein cages surrounding the nano-Al. This process is repeated to build additional protein layers on nano-Al as shown in FIG. 2A by using alternating layers of cationized and native ferritin (i.e. cationized ferritin for the third layer and native ferritin for the fourth layer), with centrifugation and resuspension steps in between each layer to remove unbound ferritins.

Alternatively, the iron oxide core of the cationized ferritin and/or the native ferritin in any layer may be replaced with AP as described in Example 1 to create a homogeneous AP-loaded ferritin-nano-Al or a heterogeneous iron oxide-AP complex.

Example 3

Characterization of Ferritin-Nano-Al

Materials and Methods

Energy dispersive X-ray (EDAX) spectroscopy was performed using an integrated EDAX detector from 0-20 keV at an angle of 15°. X-ray photoelectron spectroscopy (XPS) measurements were performed using an M-PROBE Surface Science® XPS spectrometer utilizing charge neutralization. Samples were prepared by drop-casting 10 μL of an aqueous suspension of ferritin-nano-Al onto a polished silicon wafer (Wafer World, Inc.), followed by air drying. Spectra were collected in 1 eV steps from 0-1000 eV at a spot size of 800 μm and averaged over 15 scans for standard resolution.

Ferritin binding was determined using a Q-Sense® E4 QCM-D system with flow modules. Quartz crystal microbalance (QCM) sensors coated with a 100 nm aluminum oxide film (Q-Sense, QSX-309) were cleaned by UV/ozone treatment (Novascan® PSD Pro Series Digital UV/Ozone system) for 10 minutes, immersion in a 2% SDS solution for 30 minutes, thorough rinsing with deionized water, $N_2$ drying, and another UV/ozone treatment for 10 minutes. After cleaning, sensors were mounted in QCM flow modules. Cationized ferritin (Sigma®) and native ferritin (Sigma®) at concentrations of 96 μg/mL and 56 μg/mL, respectively, in deionized water were flowed across the QCM sensors at 0.17 mL/min and monitored vs. time at the third overtone frequency for LBL assembly.

Dynamic light scattering (DLS) of multi-layer assemblies was performed on a Malvern Instruments® nano series Zetasizer® after addition of each protein cage layer. For the LBL assembled ferritin-nano-Al material, SEM and EDAX maps were obtained on a Philips XL series FEG eSEM operating at 10 kV and a working distance of 7.5 mm. For imaging and mapping, 20 μL of ferritin-nano-Al was drop-cast on a silicon wafer and mounted on an SEM puck.

Thermogravimetric analysis (TGA) and differential thermal analysis (DTA) measurements were performed in a TA Instruments® SDT Q 600. Samples (5 to 10 mg) were placed into a tared alumina crucible with an empty alumina crucible serving as the reference. All data was collected in dynamic mode under flowing argon (100 mL/min) from room temperature up to 1000° C. at a rate of 5° C./min. Control samples were prepared by mixing AP and nano-Al or iron oxide ($Fe_2O_3$) nanopowder with nano-Al at the appropriate stoichiometric ratios.

Combustion experiments were performed by placing approximately 10 mg of the respective nanocomposite powder onto a flat substrate in a vented fragmentation chamber under an air atmosphere. The powders were ignited by a butane flame from directly below. A NAC® Image Technology Memrecam® GX8 digital high speed video camera, collecting full frame, full color images at 5,000 frames per second, was used to record the combustion events.

Composition and Ferritin Binding

EDAX analysis of nano-Al particles functionalized with iron oxide-loaded cationized ferritin cages yielded a concentration of 18.2 wt % Al and 1.7 wt % Fe as measured by EDAX (data not shown). In contrast, the assembly of nano-Al with native ferritin (negatively charged) resulted in only a few protein cages being associated with the nano-Al surface by TEM and no detectable Fe (not shown). XPS measurements of nano-Al particles functionalized with AP-loaded cationized ferritin cages confirmed the presence of 0.4% Cl, 5.2% N, and 9.3 atomic % of Al (data not shown). This measurement is equivalent to a stoichiometry of approximately 440 AP molecules/protein cage and represents a fully filled cage.

Figure 4:
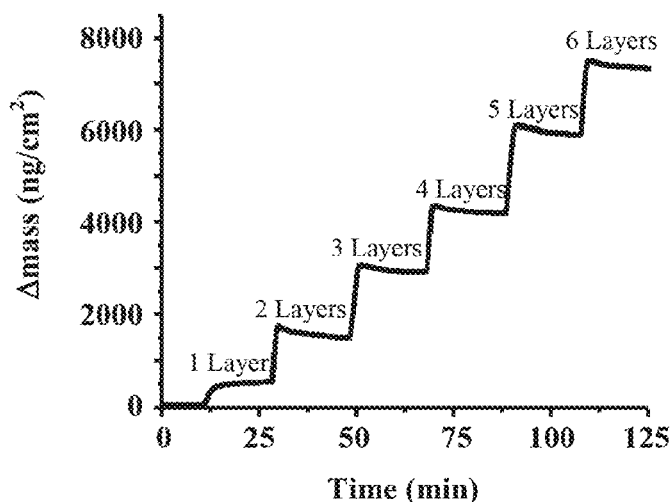
FIG. 4 is a quartz crystal microbalance plot of reactive nanocomposites comprising between one and six layers of iron oxide-loaded ferritins of equal mass.
Figure 5:
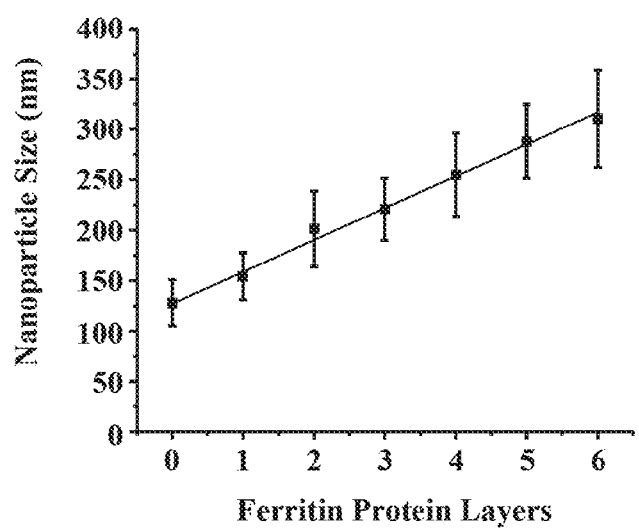
FIG. 5 is a dynamic light scattering plot of reactive nanocomposites comprising between one and six layers of iron oxide-loaded ferritins of equal mass.

FIG. 4 is a QCM plot (change in mass vs. time) of reactive nanocomposites comprising between one and six layers of iron oxide-loaded ferritins of equal mass, such as the reactive nanocomposites in FIGS. 3A-3F. The formation of alternating layers of protein cages may be seen by the step-wise increase in mass corresponding to each new layer. DLS analysis further confirmed the formation of layers of protein cages, which is reflected in FIG. 5 by an approximately linear increase in nanoparticle size with the addition of each protein layer.

Energetic Characterization of Ferritin-Nano-Al

Figure 6:
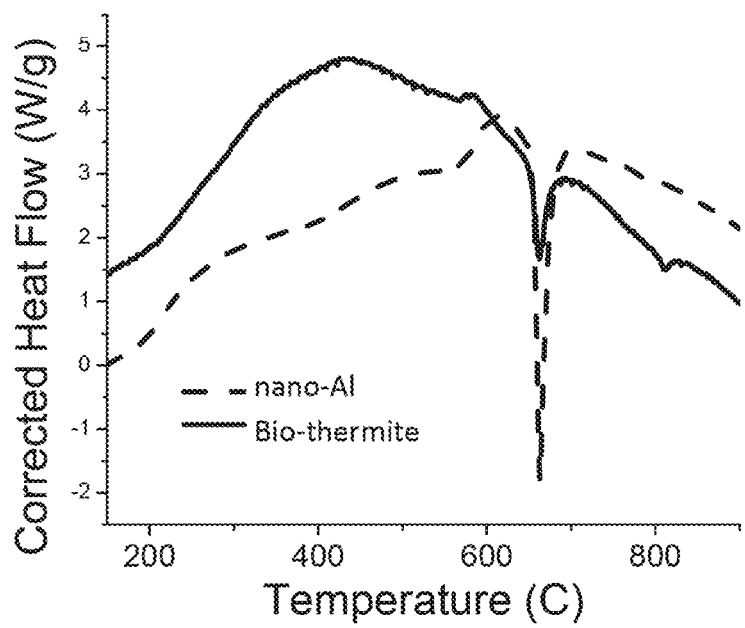
FIG. 6 is the thermogravimetric analysis (TGA)/differential thermal analysis (DTA) profile of bio-thermite and unfunctionalized nano-Al.

Initial measurements of the energetic performance of the ferritin-nano-Al materials were obtained by simultaneous TGA and DTA. FIG. 6 shows the TGA/DTA profile of bio-thermite (nano-Al functionalized with a single layer of iron oxide-loaded cationized ferritin; ———). As a baseline, the TGA/DTA profile of unfunctionalized nano-Al (– –) particles exhibited a broad exotherm occurring between 100-350° C. due to the conversion of amorphous-$Al_2O_3$ to gamma-$Al_2O_3$ and a sharp endothermic peak at 660° C. from the melting of nano-Al. This characteristic melting peak provides a means to assess how much aluminum is consumed during the course of the reaction and whether or not stoichiometric conditions are reached. For the bio-thermite sample (50 wt % Fe:50 wt % nano-Al), the exotherm appeared prior to aluminum melting, with a reaction onset at approximately 300° C. for 1.7 wt % FeO(OH) loaded ferritin. Additionally, a small endothermic peak was observed at approximately 800° C., which is also present in the TGA profile of ferritin alone (not shown). The peak at 800° C. may be attributed to a phase transition of ferrihydrite FeO(OH) to magnetite ($Fe_3O_4$).

Figure 7:
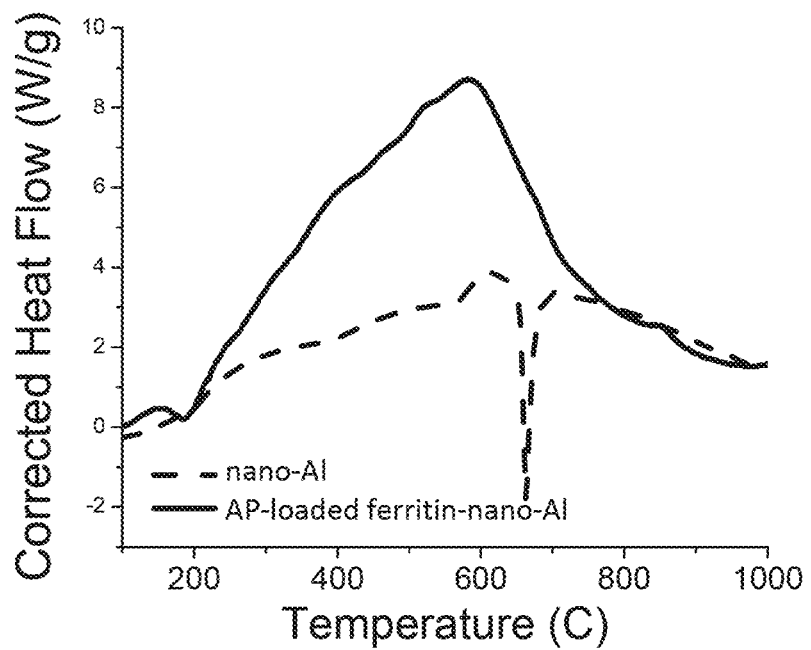
FIG. 7 is the TGA/DTA profile of AP-loaded ferritin-nano-Al and unfunctionalized nano-Al.

FIG. 7 shows the TGA/DTA profile of AP-loaded ferritin-nano-Al. Energetically, the profile of AP loaded ferritin-nano-Al (———) showed similar exothermic behavior to the bio-thermite sample in FIG. 6. However, the entire event for the AP-loaded ferritin-nano-Al was exothermic due to the complete consumption of nano-Al prior to melting. In this case, the reactants were stoichiometrically balanced using only a single layer of cationized ferritin molecules filled with AP. The TGA/DTA profile of unfunctionalized nano-Al (– –) is also shown in FIG. 7. By comparison, the addition of bulk AP recrystallized with nano-Al resulted in the thermal decomposition of AP below 200° C. and unreacted nano-Al by TGA (data not shown). The TGA/DTA profile of AP-loaded ferritin-nano-Al in FIG. 7 demonstrates the thermal stabilization of AP upon encapsulation by the ferritin protein cage and its critical role in reacting with nano-Al.

Figure 8:
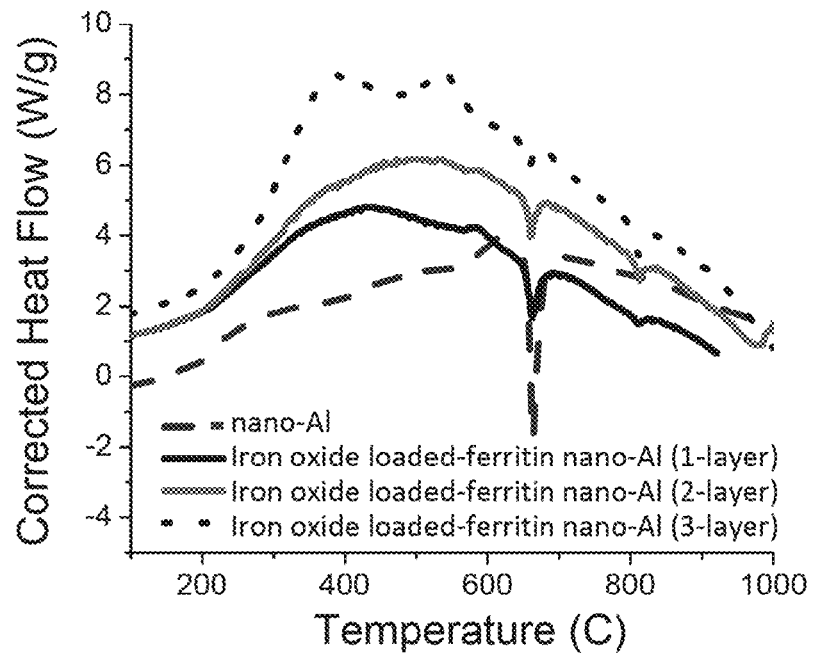
FIG. 8 is the TGA/DTA profile of unfunctionalized nano-Al and multi-layer ferritin-nano-Al containing one to four homogeneous layers of iron oxide-loaded ferritin.

FIG. 8 shows the TGA/DTA profiles of multi-layer ferritin-nano-Al containing one, two, or four homogeneous layers of iron oxide-loaded ferritin, along with the profile for unfunctionalized nano-Al (unfunctionalized nano-Al – –; 1-layer iron oxide-loaded-ferritin-nano-Al ———; 2-layer iron oxide-loaded-ferritin-nano-Al ═══; and 4-layer iron oxide-loaded-ferritin-nano-Al ·····). As compared to one another, the profiles of the multi-layer ferritin-nano-Al showed increasing exotherms as the number of layers increased from one to four, and higher consumption of nano-Al is observed by a decreased melting nano-Al peak. The exotherm size was dependent upon the weight ratio of Al to iron oxide, whereby slightly fuel rich mixtures (50:50) produced the largest exotherm.

Figure 9:
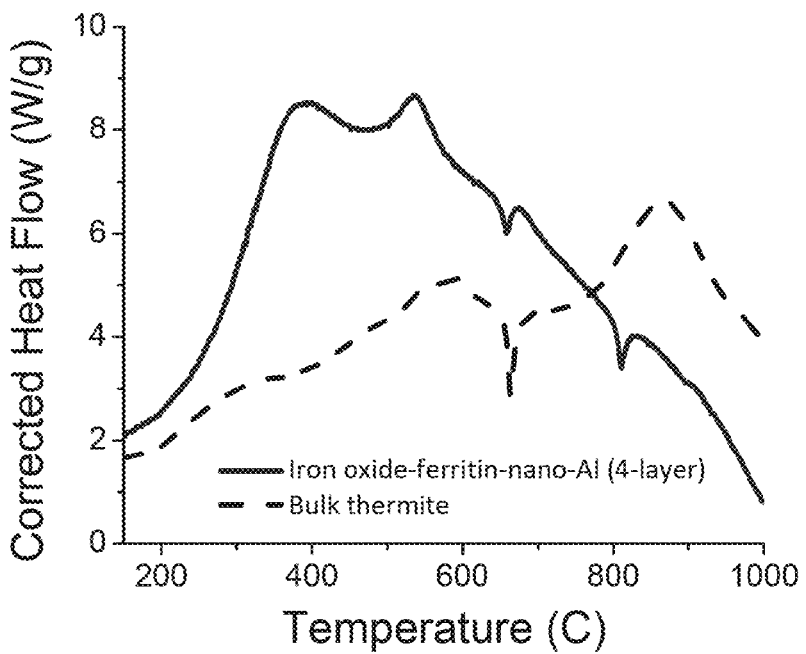
FIG. 9 is the TGA/DTA profile for four-layer ferritin-nano-Al plotted with the TGA/DTA profile generated from a bulk thermite reaction of micron- or nano-sized iron oxide particles and nano-Al particles.

For comparison, FIG. 9 shows the TGA/DTA profile for four-layer ferritin-nano-Al (———) plotted with the TGA/DTA profile generated from a bulk thermite reaction of micron- or nano-sized iron oxide particles and nano-Al particles (– –). The bulk thermite material consisted of micron size $Fe_3O_4$ powder mixed with nano-Al powder at 50 wt % Fe:50 wt % nano-Al. In FIG. 9, the exotherm for the bulk thermite reaction was not observed until 750-950° C., and the reaction released a lower amount of heat. In contrast, the bio-thermite reaction yielded larger exotherms at a lower temperature range, while also consuming more of the aluminum at near stoichiometric conditions.

Figure 10:
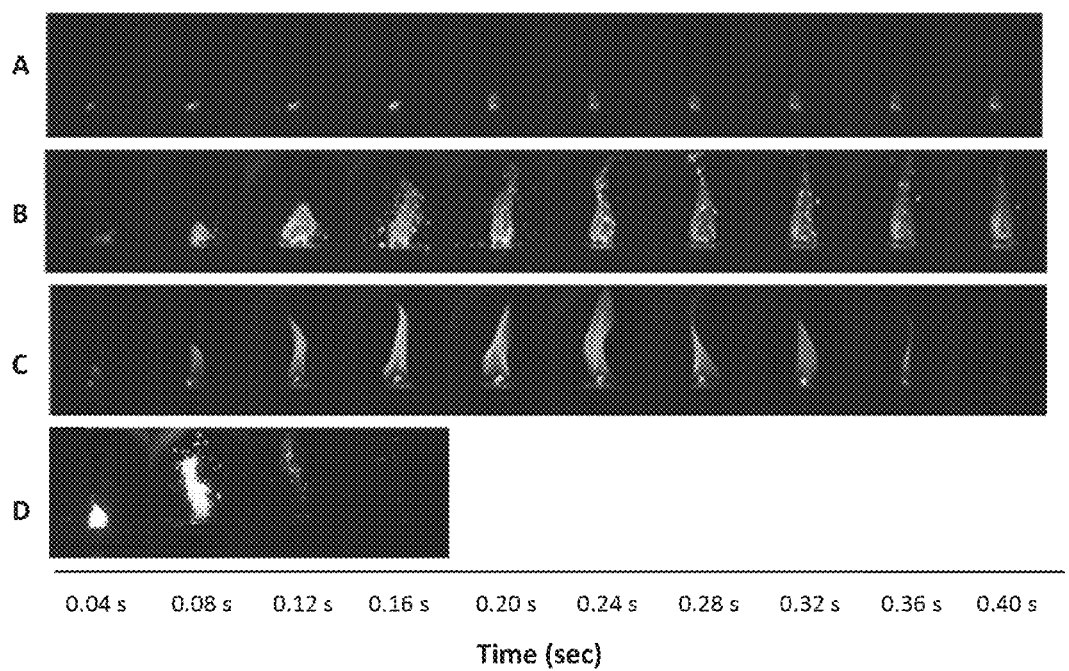
FIGS. 10A-D show the combustion characteristics of several reactive nanocomposites utilizing a high speed camera.

Finally, FIG. 10 shows the combustion characteristics of several reactive nanocomposites utilizing a high speed camera. Unlike TGA/DTA, the burn tests provide a means to qualitatively test the energetic behavior and performance of each material in a real world scenario and under normal combustion conditions. The materials were ignited using a flame from a butane torch and recorded by a high speed digital video camera during the course of combustion, followed by analysis of selected individual time frames. A two-layer apoferritin-coated nano-Al sample (no iron oxide core) shown in FIG. 10A serves as a control. The two-layer apoferritin-nano-Al powder burned slowly, yielding only a faint glow. This minimal combustion was limited by the reaction with atmospheric oxygen. However, incorporation of iron oxide into the apoferritin generated a much greater combustion event as seen FIG. 10B, which shows the combustion of a two-layer iron oxide-loaded ferritin nano-Al material. The combustion reaction of the iron oxide-loaded ferritin nano-Al material may be as follows: 2 nano-Al+3FeO(OH)→$Al_2O_3$+3Fe+3OH$^-$. The combustion event in FIG. 10B featured a large intense flame and the appearance of several sparks generated due to the flocculant nature of the electrostatically charged powder.

A significant increase in the amount of fuel (iron oxide) as in the 12-layer iron oxide-loaded ferritin-nano-Al material shown in FIG. 10C resulted in an even larger flame that burned faster. By comparison, more iron oxide was consumed in the 12-layer material, leading to faster combustion and release of more energy. Conversely, upon substitution of the iron oxide for the stronger oxidizing agent AP, the single-layer AP-loaded ferritin-nano-Al material in FIG. 10D achieved an impressive combustion that lasted a much shorter time. The combustion reaction of the AP-loaded ferritin-nano-Al material may be as follows: 8 nano-Al+3$ClO_4$→$Al_2O_3$+3Cl$^-$. In FIG. 10D, the nano-Al was rapidly consumed upon reacting with the encapsulated AP, and the reaction was essentially finished after 0.16 sec.

As described above, single- and multi-layer ferritin-nano-Al materials demonstrate enhanced reaction rates and increased energy output. The protein cages (1) offer the ability to encapsulate and thermally stabilize an inorganic material such as iron oxide or an oxidizing agent such as AP; (2) interact with and coat the surface of reactive nanometals such as nano-Al; and (3) quickly deliver the oxidizer to the reactive nanometal surface by reducing the diffusion distance and mass transport of reactants. By varying the number and composition of the protein layers, the reaction stoichiometry of the nanometal with the oxidizer may be tightly controlled in order to tailor the energetic properties to the desired application. Potentially, each protein layer may be customized with an inorganic material, oxidizing agent, molecular explosive, and/or other reactant as desired. For example, as seen in FIGS. 10A-D, the use of iron oxide-loaded ferritin nano-Al led to a slower sustained burn, which may be attractive for propellant or pyrotechnic applications, whereas the fast and intense combustion produced by the AP-ferritin-nano-Al materials may serve as a useful additive for explosive materials. Using a bio-derived route also provides the opportunity for the development of safer and more efficient combustible materials. For example, free AP is generally sensitive to shock and friction, decomposes at low temperatures, and becomes explosive when mixed with metals. Encapsulation of AP in a protein cage reduces or prevents these issues, making it safer to handle and process. Furthermore, the protein cages, due to their organic nature, may serve as gasification agents during the reaction. The heat produced during the reaction decomposes the protein cages into various carbonaceous gaseous products that will further increase the reaction pressure.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A method of making a reactive nanocomposite, comprising:
    forming a layer of a plurality of positively-charged loaded protein cages onto an outer surface of a plurality of metal nanoparticles to form the reactive nanocomposite, wherein the outer surface comprises at least one metal selected from the group consisting of Al, B, Si, Mg, Ni, Ti, and Ag, and wherein the plurality of positively-charged loaded protein cages comprise a protein cage having a first oxidizer loaded into a pore of the protein cage.

2. The method of claim 1, wherein the first oxidizer is selected from the group consisting of iron oxide and ammonium perchlorate.

3. The method of claim 1, wherein the positively-charged loaded protein cages comprise a self-assembling protein that is selected from the group consisting of cationized ferritin, heat shock proteins, capsid proteins, and ferritin-like proteins.

4. The method of claim 1, wherein the positively-charged loaded protein cages further comprise an additional reactant selected from the group consisting of a secondary chemical oxidizing agent, a non-ferric metal oxide, a molecular explosive, and a fluorescent dye taggant.

5. The method of claim 3, wherein the ferritin-like proteins are selected from the group consisting of Dps proteins and Dpr proteins.

6. The method of claim 1, further comprising:
    loading a plurality of empty protein cages with the first oxidizer to form the loaded positively-charged protein cages.

7. A method of making a multi-layered reactive nanocomposite having a charged outer surface, the method comprising the steps of:
    a) forming a layer of a plurality of positively-charged loaded protein cages onto an outer surface of a plurality of metal nanoparticles to form a reactive nanocomposite having a positively-charged outer surface;
    b) forming a layer of a plurality of i) negatively-charged loaded protein cages, or ii) negatively-charged loaded polyelectrolyte complexes onto the reactive nanocomposite having the positively-charged outer surface to form a multi-layered reactive nanocomposite having a negatively-charged outer surface; and
    c) optionally repeating step a) to form a multi-layered reactive nanocomposite having a positively-charged outer surface, or optionally repeating steps a) and b) to form the multi-layered reactive nanocomposite having the negatively-charged outer surface,
    wherein the plurality of positively-charged loaded protein cages comprise a first protein cage having a first oxidizer loaded into a pore of the first protein cage; wherein the plurality of negatively-charged loaded protein cages comprise a second protein cage having a second oxidizer loaded into a pore of the second protein cage, and wherein the plurality of negatively-charged polyelectrolyte complexes comprise a third oxidizer coated with a plurality of negatively-charged polyelectrolytes.

8. The method of claim 7, wherein the outer surface of the plurality of metal nanoparticles comprise at least one metal selected from the group consisting of Al, B, Si, Mg, Ni, Ti, and Ag.

9. The method of claim 7, wherein the first oxidizer the second oxidizer, and the third oxidizer are independently selected from the group consisting of iron oxide and ammonium perchlorate.

10. The method of claim 7, wherein the positively-charged protein cages comprise a self-assembling protein that is selected from the group consisting of cationized ferritin, heat shock proteins, capsid proteins, and ferritin-like proteins.

11. The method of claim 10, wherein the ferritin-like proteins are selected from the group consisting of Dps proteins and Dpr proteins.

12. The method of claim 7, wherein the positively-charged protein cages further comprise an additional reactant selected from the group consisting of a secondary chemical oxidizing agent, a non-ferric metal oxide, a molecular explosive, and a fluorescent dye taggant.

13. The method of claim 7, further comprising:
    coating a surface with the plurality of negatively-charged polyelectrolytes to form a coated surface; and
    assembling the reactive nanocomposite having the positively-charged outer surface or the multi-layered reactive nanocomposite having the positively-charged outer surface onto the coated surface with the plurality of negatively-charged polyelectrolytes, thereby directing assembly of the multi-layer reactive nanocomposite onto the surface.

14. The method of claim 7, further comprising:
    loading a plurality of empty first protein cages with the first oxidizer to form the loaded positively-charged protein cages;
    loading a plurality of empty second protein cages with the second oxidizer to form the loaded negatively-charged protein cages; or
    coating the third oxidizer with the plurality of negatively-charged polyelectrolytes to form the negatively-charged polyelectrolyte complexes.

15. The method of claim 7, wherein the multi-layered reactive nanocomposite comprises two to twelve layers of alternating charged layers comprising a) positively-charged loaded protein cages; and b) i) negatively-charged loaded protein cages, and/or ii) negatively-charged polyelectrolyte complexes to provide either the multi-layered reactive nanocomposite having the positively-charged outer surface, or the multi-layered reactive nanocomposite having the negatively-charged outer surface.

* * * * *